United States Patent

Mentrup et al.

Patent Number: 4,539,323
Date of Patent: Sep. 3, 1985

[54] N-[1-(4-AMINO-6,7-DIALKOXY-2-QUINAZOLINYL)-4-PIPERIDYL]-OXAZOLIDINE-2,4-DIONES

[75] Inventors: Anton Mentrup, Mainz-Kastel; Ernst-Otto Renth; Kurt Schromm, both of Ingelheim am Rhein; Wolfgang Hoefke, Wiesbaden; Wolfram Gaida, Ingelheim am Rhein, all of Fed. Rep. of Germany

[73] Assignee: Boehringer Ingelheim KG, Inglheim am Rhein, Fed. Rep. of Germany

[21] Appl. No.: 531,842

[22] Filed: Sep. 14, 1983

[30] Foreign Application Priority Data

Sep. 25, 1982 [DE] Fed. Rep. of Germany ....... 3235565

[51] Int. Cl.³ .................. A61K 31/505; C07D 413/14
[52] U.S. Cl. ..................... 514/260; 544/230; 544/250; 544/291; 544/293; 546/15; 546/209; 546/217; 546/224; 548/216; 548/227
[58] Field of Search ......... 544/291, 230, 250; 424/251

[56] References Cited

U.S. PATENT DOCUMENTS 4,309,541 1/1982 Werner ............................. 544/291

FOREIGN PATENT DOCUMENTS 2483920 12/1981 France .................. 544/291

Primary Examiner—Glennon H. Hollrah
Assistant Examiner—James H. Turnipseed
Attorney, Agent, or Firm—Hammond & Littell, Weissenberger & Dippert

[57] ABSTRACT

Compounds of the formula

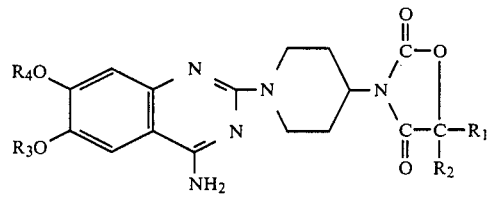

wherein
$R_1$ and $R_2$, which may be identical to or different from each other, are each independently hydrogen, straight or branched alkyl of 1 to 8 carbon atoms or arylmethyl; or
$R_1$ and $R_2$, together with each other, are $-(CH_2)_4-$ or $-(CH_2)_5-$; and
$R_3$ and $R_4$, which may be identical to or different from each other, are each independently hydrogen, straight or branched alkyl of 1 to 4 carbon atoms or arylmethyl; or
$R_3$ and $R_4$, together with each other, are $-CH_3-$ or $-CH_2-CH_2-$;

and non-toxic, pharmacologically acceptable acid addition salts thereof. The compounds as well as their salts are useful for the treatment of cardiovascular diseases, especially hypertension.

5 Claims, No Drawings

N-[1-(4-AMINO-6,7-DIALKOXY-2-QUINAZOLINYL)-4-PIPERIDYL]-OXAZOLIDINE-2,4-DIONES

This invention relates to novel piperidine derivatives, to methods of preparing these compounds, to pharmaceutical compositions containing them as active ingredients, and to methods of using them as vasodilators and hypotensives.

More particularly, the present invention relates to a novel class of piperidine derivatives represented by the formula

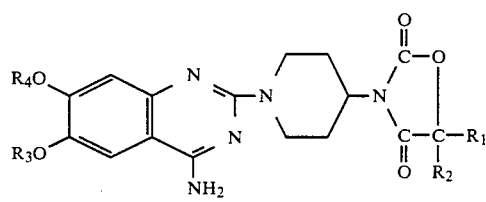

wherein
- $R_1$ and $R_2$, which may be identical to or different from each other, are each independently hydrogen, straight or branched alkyl of 1 to 8 carbon atoms or arylmethyl; or
- $R_1$ and $R_2$, together with each other, are —(CH$_2$)$_4$— or —(CH$_2$)$_5$—; and
- $R_3$ and $R_4$, which may be identical to or different from each other, are each independently hydrogen, straight or branched alkyl of 1 to 4 carbon atoms or arylmethyl; or
- $R_3$ and $R_4$, together with each other, are —CH$_3$— or —CH$_2$—CH$_2$—;

and non-toxic, pharmacologically acceptable acid addition salts thereof.

A preferred subgenus is constituted by those compounds of the formula I
wherein
- $R_1$ and $R_2$ are each independently hydrogen or alkyl of 1 to 4 carbon atoms, and
- $R_3$ and $R_4$ are both methyl, and non-toxic, pharmacologically acceptable acid addition salts thereof.

The term "arylmethyl" particularly refers to benzyl or substituted benzyl.

Depending upon whether $R_1$ and $R_2$ are identical to or different from each other, the compounds of the formula I exist as racemates, mixtures of stereoisomers or pure enantiomers.

The compounds of the formula I may be prepared by the following methods which involve known chemical synthesis principles:

METHOD A

By reacting a 4-amino-quinoxaline of the formula

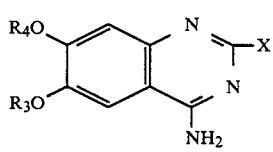

wherein $R_3$ and $R_4$ have the same meanings as in formula I, and

X is chlorine, bromine or (alkyl of 1 to 4 carbon atoms)thio, with a piperidine derivative of the formula

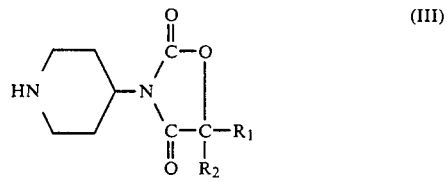

wherein $R_1$ and $R_2$ have the same meanings as in formula I.

The reaction is advantageously performed in the presence of an acid-binding agent, for example, an alkali metal carbonate such as sodium carbonate or potassium carbonate, or an amine such as tripropylamine, or 2 equivalents or an excess of reactant III, and preferably at elevated temperatures, most advantageously in an inert solvent at the reflux temperature of the reaction mixture.

The starting compounds of the formula II are either known compounds or may be prepared by methods described in the literature.

The starting compounds of the formula III may, for example, be prepared pursuant to the following reaction sequence:

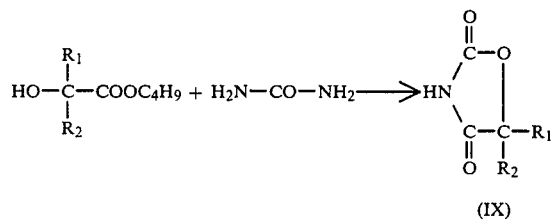

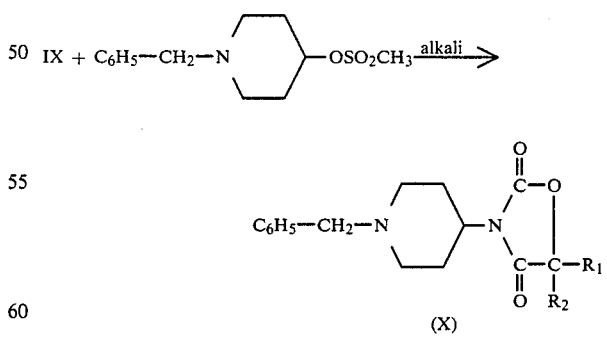

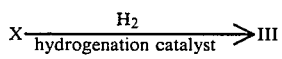

METHOD B

By reacting a compound of the formula

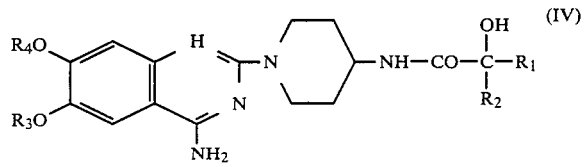 (IV)

wherein $R_1$, $R_2$, $R_3$ and $R_4$ have the meanings previously defined, with a dialkyl carbonate of the formula

 (V)

wherein R and R', which may be identical to or different from each other, are each straight or branched alkyl of 1 to 6 carbon atoms.

The reaction is advantageously carried out at elevated temperatures in the presence of a small amount of sodium hydride and a lower alkanol such as ethanol. The dialkyl carbonate is preferably supplied in sufficient excess to serve simultaneously as a solvent medium for the reaction, so that no separate inert solvent is required.

The starting compounds for this method are either known compounds or may be prepared by known methods.

For example, the starting compounds of the formula IV can be obtained by reacting a compound of the formula

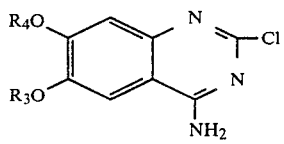

wherein $R_3$ and $R_4$ have the meanings previously defined, with a compound of the formula

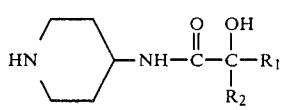

wherein $R_1$ and $R_2$ have the meanings previously defined.

METHOD C

By reacting a carbamate of the formula

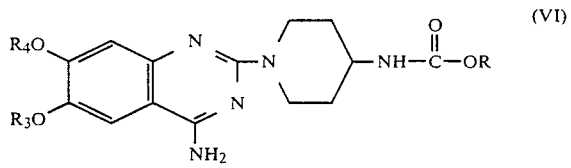 (VI)

wherein
 $R_3$ and $R_4$ have the meanings previously defined, and
 R is straight or branched alkyl of 1 to 6 carbon atoms, with a hydroxycarboxylic acid ester of the formula

 (VII)

wherein
 $R_1$ and $R_2$ have the meanings previously defined, and
 R' is straight or branched alkyl of 1 to 6 carbon atoms.

The reaction is carried out at elevated temperatures in a high-boiling-point inert solvent such as ethylene glycol dimethyl ether and in the presence of a small amount of sodium hydride.

The starting compounds for this method are either known compounds or may be prepared by known methods.

METHOD D

By reacting a compound of the formula

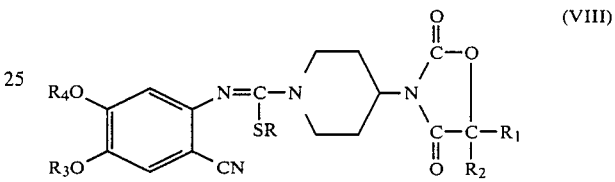 (VIII)

wherein R, $R_1$, $R_2$, $R_3$ and $R_4$ have the meanings previously defined, with ammonium chloride and formamide at moderately elevated temperatures.

The formamide is preferably provided in sufficient excess to serve simultaneously as the solvent medium for the reaction, thereby obviating the necessity of providing a separate inert solvent.

The starting compounds of the formula VIII can be obtained by known methods, for example by the following reaction sequence:

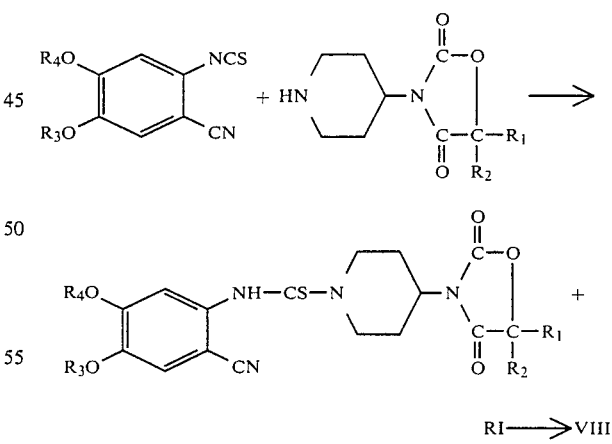

RI ⟶ VIII

When $R_1$ and $R_2$ in formula I are different, the mixtures of enantiomers obtained as end products be methods A to D may be separated by conventional methods. However, it is also possible to use optically active starting compounds.

The compounds embraced by formula I are basic and therefore form addition salts with inorganic or organic acids. Examples of non-toxic, pharmacologically acceptable acid addition salts are those formed with hydrochloric acid, methanesulfonic acid, hydrobromic acid, sulfuric acid, formic acid, acetic acid, succinic acid, glycolic acid, citric acid, maleic acid, nicotinic acid, pamoic acid, phenylacetic acid, benzoic acid, cyclohexylsulfamic acid or toluenesulfonic acid.

The following examples illustrate the present invention and will enable others skilled in the art to understand it more completely. It should be understood, however, that the invention is not limited solely to the particular examples given below.

EXAMPLE 1

N-[1-(4-Amino-6,7-dimethoxy-2-quinazolinyl)-4-piperidyl]-oxazolidine-2,4-dione

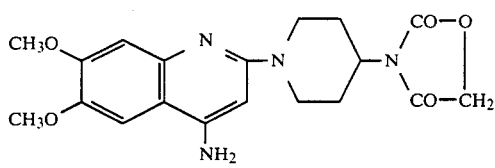

2.4 g of 2-Chloro-4-amino-6,7-dimethoxy-quinazoline and 2.32 g of N-(4-piperidyl)-oxazolidin-2,4-dione hydrochloride was refluxed with 3 g of tri-n-propylamine in 50 ml of ethyl glycol for 2 hours. The product which precipitated upon cooling was isolated in the form of the hydrochloride with a yield of 4 g after the addition of 50 ml of ether. To convert it into the base, the hydrochloride was suspended in 25 ml of water and mixed with 15 ml of aqueous ammonia. The base, isolated with a yield of 95.5% had a melting point of 230° C. after being recrystallized from methanol.

After the addition of the calculated quantity of methanesulfonic acid, the methanesulfonate (M.p. 307° C.) crystallized out of the base which had been dissolved in methanol with heating.

The N-(4-piperidyl)-oxazolidin-2,4-dione used as starting material was prepared by hydrogenation of 12 g of N-[4-(1-benzyl-piperidyl)]-oxazolidine-2,4-dione in 400 ml of methanol after the addition of 12 ml of a 13.6% methanolic hydrochloric acid solution in the presence of a palladium-on-charcoal as the catalyst. The yield of the substance isolated in the form of the hydrochloride was 72% (M.p. 287° C.).

The N-[4-(1-benzyl-piperidyl)]-oxazolidin-2,4-dione used as starting material was obtained by the addition of 30 g of 4-methanesulfonyloxy-1-benzyl-piperidine to a solution of 10.1 g of oxazolidin-2,4-dione and 4.2 g of sodium hydride in 120 ml of hexametapol. After 3 hours' reaction, the product was isolated with a yield of 45% in the form of the maleate (M.P. 206° C.).

The following compounds of the formula I were obtained analogous to Example 1:

TABLE I

| Example No. | $R_1$ | $R_2$ | $R_3$ | $R_4$ | M.p. [°C.] Base | M.p. [°C.] Salt |
|---|---|---|---|---|---|---|
| 2 | $CH_3$ | $CH_3$ | $CH_3$ | $CH_3$ | 223 | 293 ($CH_3SO_3H$) |
| 3 | $CH_3$ | H | $CH_3$ | $CH_3$ | | 280 (HCl) |
| 4 | $CH_3$ | $C_2H_5$ | $CH_3$ | $CH_3$ | 135 | 288 ($CH_3SO_3H$) |
| 5 | $n-C_4H_9$ | H | $CH_3$ | $CH_3$ | 80 | 230 ($CH_3SO_3H$) |
| 6 | —$(CH_2)_4$— | | $CH_3$ | $CH_3$ | 140 | 295 ($CH_3SO_3H$) |
| 7 | $CH(CH_3)_2$ | H | $CH_3$ | $CH_3$ | | 272 |
| 8 | $C_2H_5$ | H | $CH_3$ | $CH_3$ | | 298 ($CH_3SO_3H$) |
| 9 | $n-C_3H_7$ | H | $CH_3$ | $CH_3$ | | 243 ($CH_3SO_3H$) |
| 10 | $C_6H_5-CH_2$ | H | $CH_3$ | $CH_3$ | | 284 (HCl) |

EXAMPLE 11

(a)

2-[4-(3-Methyl-2-hydroxy)-butyramido]-piperid-1-yl-4-amino-6,7-dimethoxy-quinazoline A mixture of 2.9 g (0.012 mol) of 2-chloro-4-amino-6,7-dimethoxy-quinazoline-(1), 2.4 g (0.012 mol) of 4-(2-hydroxy-3-methyl-butyramido)-piperidine, 2.3 ml (0.012 mol) of tri-n-propylamine and 40 ml of ethyl glycol was refluxed for 2 hours. The reaction mixture was then concentrated by evaporation, and the oily residue was taken up in semi-concentrated ammonia water and ethyl acetate. The ethyl acetate phase was dried and concentrated by evaporation, 4.6 g of the title compound were isolated.

(b)

1-[1-(4-Amino-6,7-dimethoxy-2-quinazolinyl)-4-piperidyl]-5-isopropyl-2,4-oxazolidindione methane sulfonate A suspension of 2.0 g (0.005 mol) of the compound obtained in (a), 4 ml (0.033 mol) of diethylcarbonate, 40 mg (0.001 mol) of a 57.5% sodium hydride dispersion and 0.5 ml of ethanol was reacted for 5 hours at an external temperature of 170° C. Meanwhile, the ethanol slowly distilled off. The mixture was cooled to room temperature and mixed with ice water. After it had been shaken with ethyl acetate, it was washed again with water, then dried and concentrated by evaporation. The oily residue was combined with methanesulfonic acid. After recrystallization, the salt had a melting point of 272° C.

The following compounds of the formula I were obtained analogous to Example 11:

TABLE II

| Example No. | $R_1$ | $R_2$ | $R_3$ | $R_4$ | M.p. [°C.] Base | M.p. [°C.] Salt |
|---|---|---|---|---|---|---|
| 12 | $CH_3$ | $CH_3$ | $CH_3$ | $CH_3$ | 223 | 293 ($CH_3SO_3H$) |
| 13 | $CH_3$ | H | $CH_3$ | $CH_3$ | | 280 (HCl) |
| 14 | $CH_3$ | $C_2H_5$ | $CH_3$ | $CH_3$ | 135 | 288 ($CH_3SO_3H$) |
| 15 | $n-C_4H_9$ | H | $CH_3$ | $CH_3$ | 80 | 230 ($CH_3SO_3H$) |
| 16 | —$(CH_2)_4$— | | $CH_3$ | $CH_3$ | 140 | 295 ($CH_3SO_3H$) |
| 17 | H | H | $CH_3$ | $CH_3$ | | 307 ($CH_3SO_3H$) |
| 18 | $C_2H_5$ | H | $CH_3$ | $CH_3$ | | 298 ($CH_3SO_3H$) |
| 19 | $n-C_3H_7$ | H | $CH_3$ | $CH_3$ | | 243 ($CH_3SO_3H$) |
| 20 | $C_6H_5-CH_2$ | H | $CH_3$ | $CH_3$ | | 284 (HCl) |

EXAMPLE 21

1-[1-(4-Amino-6,7-dimethoxy-2-quinazolinyl)-4-piperidyl]-5-isopropyl-2,4-oxazolidindione methanesulfonate A mixture of 0.38 g (0.001 mol) of 2-(4-ethylcarbamido-piperidyl)-4-amino-6,7-dimethoxy-quinazoline, 0.13 g (0.001 mol) of methyl 2-hydroxy-3-methyl-butyrate, 2 ml of diglyme and 0.04 g (0.001 mol) of a 57% sodium hydride dispersion was kept at an internal temperature of 120° C. for one hour. After cooling, ice water was added, and the mixture was extracted with ethyl acetate. The ethyl acetate phase was washed with water, dried and concentrated by evaporation. The methanesulfonate, which melted at 272° C. after recrystallization, was prepared from the oily residue which amounted to 0.6 g.

The following compounds of the formula I were obtained analogous to Example 21:

TABLE III

| Example No. | $R_1$ | $R_2$ | $R_3$ | $R_4$ | M.p. [°C.] Base | M.p. [°C.] Salt |
|---|---|---|---|---|---|---|
| 22 | $CH_3$ | $CH_3$ | $CH_3$ | $CH_3$ | 223 | 293 ($CH_3SO_3H$) |
| 23 | $CH_3$ | H | $CH_3$ | $CH_3$ | | 280 (HCl) |
| 24 | $CH_3$ | $C_2H_5$ | $CH_3$ | $CH_3$ | | 288 ($CH_3SO_3H$) |
| 25 | n-$C_4H_9$ | H | $CH_3$ | $CH_3$ | 80 | 230 ($CH_3SO_3H$) |
| 26 | —$(CH_2)_4$— | | $CH_3$ | $CH_3$ | 140 | 295 ($CH_3SO_3H$) |
| 27 | H | H | $CH_3$ | $CH_3$ | | 307 ($CH_3SO_3H$) |
| 28 | $C_2H_5$ | H | $CH_3$ | $CH_3$ | | 298 ($CH_3SO_3H$) |
| 29 | n-$C_3H_7$ | H | $CH_3$ | $CH_3$ | | 243 ($CH_3SO_3H$) |
| 30 | $C_6H_5$—$CH_2$ | H | $CH_3$ | $CH_3$ | | 284 (HCl) |

EXAMPLE 31

(a)

3-[1-(2-Nitrilo-4,5-dimethoxy-phenyl-thiocarbamido)-4-piperidyl]-5-isopropyl-2,4-oxazolidindione A solution of 5.6 g (0.0254 mol) of 3,4-dimethoxy-6-isothiocyanato-benzonitrile in 32 ml of ethyl acetate was added dropwise, at 0° to 5° C., to a solution of 5.8 g (0.0256 mol) of 4-(5-isopropyl-2,4-oxazolidindion-3-yl)-piperidine in 33 ml of ethyl acetate over a period of 20 minutes. The mixture was allowed to react for 3 hours at 0° C. and then for 13 hours at room temperature, and was then suction-filtered. Yield: 10.0 g (88.2% of theory), light brown crystals, m.p. 201° C.

(b)

3-[1-(2-Nitrilo-4,5-dimethoxy-phenyl-methyl-thio-(formamido)-4-piperidyl]-5-isopropyl-2,4-oxazolidindione 2.8 ml (0.0448 mol) of methyl iodide were added to a stirred mixture of 10.0 g (0.0224 mol) of the compound obtained in (a) in 90 ml of ethyl acetate. After 5 hours' stirring at 60° C. the mixture was allowed to stand overnight. It was extracted with 2N sodium hydroxide, and then the ethyl acetate phase was washed twice with water, dried and concentrated by evaporation.

Yield: 7.9 g (76.6% of theory); dark red oil.

(c)

1-[1-(4-Amino-6,7-dimethoxy-2-quinazolinyl)-4-piperidyl]-5-isopropyl-2,4-oxazolidindione methane sulfonate A mixture of 3.5 g (0.0076 mol) of the compound obtained in (b), 8.0 g (0.15 mol) of ammonium chloride and 35 ml of formamide was stirred for 2 hours at 120° C. in a nitrogen atmosphere. After the addition of ice water, the product was suction-filtered. To purify them, the crystals were dissolved in ethyl acetate, and the solution was extracted successively with concentrated ammonia water and twice with water, and then dried and concentrated by evaporation.

The following compounds of the formula I were obtained analogous to Example 31:

TABLE IV

| Example No. | $R_1$ | $R_2$ | $R_3$ | $R_4$ | M.p. [°C.] Base | M.p. [°C.] Salt |
|---|---|---|---|---|---|---|
| 32 | $CH_3$ | $CH_3$ | $CH_3$ | $CH_3$ | 223 | 293 ($CH_3SO_3H$) |
| 33 | $CH_3$ | H | $CH_3$ | $CH_3$ | | 280 (HCl) |
| 34 | $CH_3$ | $C_2H_5$ | $CH_3$ | $CH_3$ | 135 | 288 ($CH_3SO_3H$) |
| 35 | n-$C_4H_9$ | H | $CH_3$ | $CH_3$ | 80 | 230 ($CH_3SO_3H$) |
| 36 | —$(CH_2)_4$— | | $CH_3$ | $CH_3$ | 140 | 295 ($CH_3SO_3H$) |
| 37 | H | H | $CH_3$ | $CH_3$ | | 307 ($CH_3SO_3H$) |
| 38 | $C_2H_5$ | H | $CH_3$ | $CH_3$ | | 298 ($CH_3SO_3H$) |
| 39 | n-$C_3H_7$ | H | $CH_3$ | $CH_3$ | | 243 ($CH_3SO_3H$) |
| 40 | $C_6H_5$—$CH_2$ | H | $CH_3$ | $CH_3$ | | 284 (HCl) |

The crystals (melting point 125° C.) were dissolved in ethanol, methanesulfonic acid was added and the product was suction-filtered. Yield: 1.8 g, crystals, m.p. 272° C.

The compounds of the present invention, that is, those embraced by formula I and their non-toxic, pharmacologically acceptable acid addition salts, have useful pharmacodynamic properties. More particularly, they exhibit vasodilating activity in warm-blooded animals such as rats, and are therefore useful for the treatment of cardiac/circulatory diseases, especially high blood pressure.

The surprisingly strong and long-lasting hypotensive effect can be demonstrated, for example, by tests on conscious SH-rats after oral administration or on anesthetized rabbits after intravenous administration. A marked α-adrenolytic effect can be demonstrated on the rats' seminal vesicle. Compared with the known α-adrenolytics phentolamine and prazosin, the compounds of the present invention have a superior activity.

The long-lasting hypotensive effect was tested on rats, for example. After oral administration of 10 mg/kg of the compounds of Examples 4, 5, 7 and 8 (Table I) on five successive days, a lowering of blood pressure of more than 20 mm Hg was still observed as much as six hours after administration.

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds of the present invention is from 0.0014 to 0.71 mgm/kg body weight, preferably 0.0071 to 0.14 mgm/kg body weight.

The compounds of the present invention are also suitable for use in combination with one or more other pharmaceutical substances. Combinations with substances having a cardiac/circulatory effect or a hypotensive effect are particularly desirable. Particular mention should be made of diuretics, β-blockers, vasodilators, sympathicolytics and converting enzyme blockers. The following are examples of active substances in these categories:

| | |
|---|---|
| Acebutolol | Labetalol |
| Allopurinol | Metolazone |
| α-Methyldopa | Metoprolol |
| Alprenolol | Minoxidil |
| Atenolol | Nadolol |
| Bumetamide | Sodium nitroprusside |
| Captopril | Oxprenolol |
| Chlorthalidone | Phentolamine |
| Clonidine | Pindolol |
| Debrisoquine | Prazosin |
| Diazoxide | Propanolol |
| Dihydralazine | Reserpine |
| Etacrynic acid | Ro 12-4713 Larovasin |
| Furosemide | Sotalol |
| Guanfacine | Tienilic acid |
| Hydrochlorothiazide | Timolol |
| Indapamid | Verapamil |

The following examples illustrate a few pharmaceutical compositions comprising a compound of the present invention as an active ingredient and represent the best modes contemplated of using the invention. The parts are parts by weight unless otherwise specified.

EXAMPLE 41

Tablets

The tablet composition is compounded from the following ingredients:

| | |
|---|---|
| N—[1-(4-amino-6,7-dimethoxy-2-quinazolinyl)-4-piperidyl]-oxazolidine-2,4-dione hydrochloride | 1 parts |
| Colloidal silicic acid | 10 parts |
| Potato starch | 60 parts |
| Lactose | 117 parts |
| Polyvinyl pyrrolidone | 6 parts |
| Sodium cellulose glycolate | 4 parts |
| Magnesium stearate | 2 parts |
| Total | 200 parts |

PREPARATION

The ingredients are compounded in conventional manner, and the composition is compressed into 200 mg-tablets, each of which contains 1 mg of the active ingredient.

EXAMPLE 42

Capsules

The capsule filler composition is compounded from the following ingredients:

| | |
|---|---|
| N—[1-(4-amino-6,7-dimethoxy-2-quinazolinyl)-4-piperidyl]-5-isopropyl-oxazolidine-2,4-dione methanesulfonate | 5 parts |
| Corn starch | 295 parts |
| Total | 300 parts |

PREPARATION

The finely divided ingredients are intimately admixed with each other, and 300 mg-portions of the mixture are filled into gelatin capsules of suitable size. Each capsule contains 5 mg of the active ingredient.

Any one of the other compounds embraced by formula I or a non-toxic, pharmacologically acceptable acid addition salt thereof may be substituted for the particular active ingredient in Examples 41 and 42. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

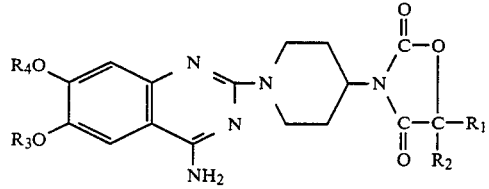

wherein
$R_1$ and $R_2$ are each independently hydrogen, straight or branched alkyl of 1 to 8 carbon atoms or benzyl; or
$R_1$ and $R_2$, together with each other, are —(CH$_2$)$_4$— or —(CH$_2$)$_5$—; and
$R_3$ and $R_4$ are each independently hydrogen, straight or branched alkyl of 1 to 4 carbon atoms or benzyl; or
$R_3$ and $R_4$, together with each other, are —CH$_3$— or —CH$_2$—CH$_2$—;
or a non-toxic, pharmacologically acceptable acid addition salt thereof.

2. A compound of claim 1,
where
$R_1$ and $R_2$ are each independently hydrogen or alkyl of 1 to 4 carbon atoms, and
$R_3$ and $R_4$ are methyl,
or a non-toxic, pharmacologically acceptable acid addition salt thereof.

3. A compound of claim 1, which is N-[1-(4-amino-6,7-dimethoxy-2-quinazolinyl)-4-piperidyl]-5-isopropyloxazolidine-2,4-dione or a non-toxic, pharmacologically acceptable acid addition salt thereof.

4. An hypotensive pharmaceutical composition consisting essentially of an inert pharmaceutical carrier and an effective hypotensive amount of a compound of claim 1.

5. The method of lowering the blood pressure of a warm-blooded animal in need thereof, which comprises perorally or parenterally administering to said animal an effective hypotensive amount of a compound of claim 1.

* * * * *